(12) United States Patent
Ota et al.

(10) Patent No.: US 8,268,360 B2
(45) Date of Patent: Sep. 18, 2012

(54) MOTOR FUNCTION IMPROVER

(75) Inventors: Noriyasu Ota, Tochigi (JP); Satoshi Haramizu, Tochigi (JP); Takatoshi Murase, Tochigi (JP)

(73) Assignee: Kao Corporation, Tokyo (JP)

( * ) Notice: Subject to any disclaimer, the term of this patent is extended or adjusted under 35 U.S.C. 154(b) by 148 days.

(21) Appl. No.: 12/869,082

(22) Filed: Aug. 26, 2010

(65) Prior Publication Data

US 2012/0052129 A1    Mar. 1, 2012

(51) Int. Cl.
*A61K 35/12* (2006.01)
(52) U.S. Cl. ........................................................ 424/520
(58) Field of Classification Search .................... 424/520
See application file for complete search history.

(56) References Cited

U.S. PATENT DOCUMENTS

2007/0160698 A1    7/2007    Waga et al.

FOREIGN PATENT DOCUMENTS

| JP | A-2002-065212 | 3/2002 |
| JP | A-2005-089384 | 4/2005 |
| JP | A-2007-112793 | 5/2007 |
| JP | A-2007-246404 | 9/2007 |
| JP | A-2007-320901 | 12/2007 |
| JP | A-2010-059155 | 3/2010 |
| WO | WO 2005/074962 A1 | 8/2005 |

OTHER PUBLICATIONS

Anderson, F. et al., "Nutritional Therapy for Adults with Renal Disease," J Am. Medical Assoc. 223: 68-72 (Jan. 1973), American Medical Association, Chicago, IL.

*Primary Examiner* — Raymond Henley, III
(74) *Attorney, Agent, or Firm* — Sterne, Kessler, Goldstein & Fox, P.L.L.C.

(57) ABSTRACT

The present invention relates to a motor function improving method, including administering or taking a fat globule membrane component.

18 Claims, 3 Drawing Sheets

*P<0.05 (Fisher's PLSD vs Cont)

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial sequence
<220> FEATURE:
```

<223> OTHER INFORMATION: Oligonucleotide from 36B4, as forward PCR
      primer

<400> SEQUENCE: 1
gacatcacag agcaggccct                                              20

<210> SEQ ID NO 2
<211> LENGTH: 20
<212> TYPE: DNA
<213> ORGANISM: Artificial sequence
<220> FEATURE:
<223> OTHER INFORMATION: Oligonucleotide from 36B4, as reverse PCR
      primer from 36B4

<400> SEQUENCE: 2
tctccacaga caatgccagg                                              20

<210> SEQ ID NO 3
<211> LENGTH: 17
<212> TYPE: DNA
<213> ORGANISM: Artificial sequence
<220> FEATURE:
<223> OTHER INFORMATION: Oligonucleotide from Na-K pump beta 1, as
      forward PCR primer

<400> SEQUENCE: 3
gctggccgtg cagttca                                                 17

<210> SEQ ID NO 4
<211> LENGTH: 19
<212> TYPE: DNA
<213> ORGANISM: Artificial sequence
<220> FEATURE:
<223> OTHER INFORMATION: Oligonucleotide from Na-K pump beta 1, as
      reverse PCR primer

<400> SEQUENCE: 4
cactcgacgc ggatttcag                                               19

<210> SEQ ID NO 5
<211> LENGTH: 20
<212> TYPE: DNA
<213> ORGANISM: Artificial sequence
<220> FEATURE:
<223> OTHER INFORMATION: Oligonucleotide from SERCA2, as forward PCR
      primer

<400> SEQUENCE: 5
tactgaccct gtccctgacc                                              20

<210> SEQ ID NO 6
<211> LENGTH: 20
<212> TYPE: DNA
<213> ORGANISM: Artificial sequence
<220> FEATURE:
<223> OTHER INFORMATION: Oligonucleotide from SERCA2, as reverse PCR
      primer

<400> SEQUENCE: 6
caccaccact cccatagctt                                              20

MOTOR FUNCTION IMPROVER

REFERENCE TO SEQUENCE LISTING SUBMITTED ELECTRONICALLY

The content of the electronically submitted substitute sequence listing, file name: 25370360000.TXT; Size: 1555 bytes; and Date of Creation: Oct. 15, 2010, filed herewith, is incorporated herein by reference in its entirety.

BACKGROUND OF THE INVENTION

1. Field of the Invention

The present invention relates to a drug, a food, and the like which exhibit a motor function improving effect.

In general, for improving motor ability such as muscle strength, exercise training and well-balanced nutrition are thought to be important. Recently, sports lovers and athletes have attempted to employ not only training but also nutrition with supplements and the like to improve their muscle strength more efficiently (Patent Document 1).

However, there is concern that training with excess intake of certain proteins or amino acids may have an adverse effect on the kidney function and the like (Non-Patent Document 1).

On the other hand, in persons other than sports lovers or athletes, unreasonable restriction of diets may cause problems such as insufficient internal supply of nutritional components, decrease in skeletal muscle, deterioration in motor functions such as muscle strength and endurance, and further fatigue associated with the deterioration in motor functions.

Therefore, in not only sports lovers and athletes who aim to improve their performance but also ordinary persons who intend to reduce their obesity, efficient motor function improvement methods are being desired.

From such a viewpoint, components having a motor function improving effect have been searched for. Consequently, for example, improvement in endurance by tea catechin (Patent Document 2) and improvement in muscle strength by polymer polyphenol derived from a fruit (Patent Document 3) have been reported.

A fat globule membrane component is a membrane that coats milk fat globules secreted from the mammary gland, and has many physiologic functions as a food for newborn animals in addition to the function of dispersing fat into milk. Examples of known physiological functions include a promoting effect on the increase and/or inhibiting effect on the decrease in a blood adiponectin level (Patent Document 4), a learning ability improving effect (Patent Document 5), and a sialomucin secretion promoting effect (Patent Document 6).

However, effects of the fat globule membrane component on motor functions such as endurance or fatigue have not been known.

2. Prior Art Document

[Patent Document]

[Patent Document 1] JP-A-2002-065212

[Patent Document 2] JP-A-2005-89384

[Patent Document 3] WO 2005/074962 pamphlet

[Patent Document 4] JP-A-2007-320901

[Patent Document 5] JP-A-2007-246404

[Patent Document 6] JP-A-2007-112793

[Non-Patent Document]

[Non-Patent Document 1] Anderson et al., JAMA, 223: 68-72. 1973

SUMMARY OF THE INVENTION

The present invention relates to the following (1) to (6):

(1) A motor function improving method, including administering or taking a fat globule membrane component.

(2) An endurance improving method, including administering or taking a fat globule membrane component.

(3) An anti-fatigue method, including administering or taking a fat globule membrane component.

(4) A muscle strength improving method, including administering or taking a fat globule membrane component.

(5) A glycogen accumulation promoting method, including administering or taking a fat globule membrane component.

(6) A muscle pump function improving method, including administering or taking a fat globule membrane component.

DETAILED DESCRIPTION OF THE INVENTION

Figure 1:
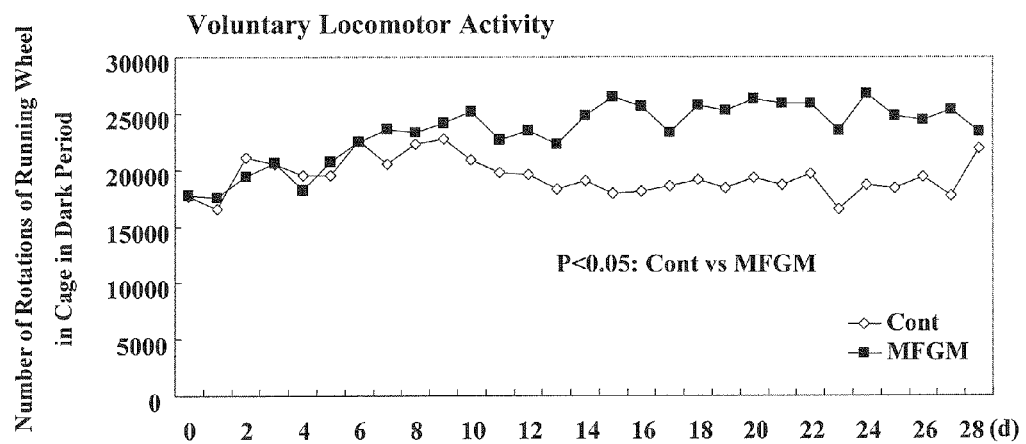
FIG. 1 is a graph showing a transition of the voluntary locomotor activity. Cont represents a normal diet group, and MFGM represents a 3.5% fat globule membrane component diet group.

The present invention relates to providing a drug, a quasi drug, a food and a feed that are commonly consumed in diet, have high safety, and exhibit an excellent motor function improving action, endurance improving action, anti-fatigue action, muscle strength improving action, glycogen accumulation promoting action, or muscle pump function improving action.

The present inventors have searched for components which are effective in improving physical functions, and have found that the fat globule membrane component among components derived from milk has an effect of a motor function improving action, an endurance improving action, an anti-fatigue action, a muscle strength improving action, a glycogen accumulation promoting action or a muscle pump function improving action, and that the component is useful as drugs, quasi drugs, foods and feeds that can exhibit such effects.

According to the method of the present invention, motor function improvement, endurance improvement, anti-fatigue, muscle strength improvement, glycogen accumulation promotion, or muscle pump function improvement can be efficiently achieved in exercises as well as broadly-defined exercises including a daily action and labor.

Examples of the fat globule membrane component in the present invention include a component which coats fat globules in milk, and a membrane component mixture derived therefrom.

It is known that the fat globule membrane component is contained much in a fraction which contains milk complex lipid such as butter milk and butter serum with high content, and about half the dry amount of the fat globule membrane component is composed of lipid (S. Miura, FOOD STYLE21, 2009). It is known that as the lipid, triglyceride and phospholipids (for example, sphingophospholipid and glycerophospholipid) are contained in large amounts, and in addition, glycosphingolipid (for example, glucosylceramide and ganglioside) are contained (Keenan, Applied Sci, 1983). Furthermore, as components other than lipids, it is known that a protein such as glycoprotein called milk mucin (Mather, Biochim Biophys Acta, 1978) is contained.

Examples of phospholipids contained in the fat globule membrane component of the present invention include sphingophospholipids such as sphingomyelin, and glycerophospholipids such as phosphatidylcholine and phosphatidylethanolamine. Among them, the fat globule membrane component preferably includes sphingomyelin, which is a characteristic phospholipid derived from milk.

The content of lipid in the fat globule membrane component of the present invention is not particularly limited but the content is preferably from 20 to 100% by mass and more preferably from 50 to 90% by mass in terms of dry matter.

The content of phospholipid in the fat globule membrane component is not particularly limited but the content is preferably from 10 to 100% by mass, more preferably from 15 to 85% by mass, and even more preferably from 20 to 70% by mass in terms of dry matter.

The content of each phospholipid in the fat globule membrane component of the present invention is not particularly limited but, for example, the content of sphingomyelin in the fat globule membrane component is preferably from 1 to 50% by mass, more preferably from 2 to 30% by mass, even more preferably from 3 to 25% by mass, and even more preferably from 4 to 20% by mass in terms of dry matter.

As the fat globule membrane component of the present invention, components obtained from milk raw material and the like by method of preparing various fat globule membrane components, such as a centrifugation method and an organic solvent extraction method may be used. Furthermore, components whose purity is increased by purification by techniques such as dialysis, ammonium sulfate fractionation, gel filtration, isoelectric precipitation, ion-exchange chromatography, and solvent fractionation may be used.

Examples of the milk raw materials of the fat globule membrane component of the present invention include cow milk and goat milk. Among the milk, a fat globule membrane component derived from cow milk is particularly preferable because it is commonly consumed in diet, and that with high purity and low price is commercially available.

Furthermore, the milk raw materials include not only raw milk, nonfat milk, and processed milk but also dairy products. Examples of the dairy products include butter milk, butter oil, butter serum, and whey protein concentrate (WPC).

The fat globule membrane component of the present invention can be prepared by a method of extracting, for example, milk, and daily products such as whey protein concentrate (WPC), butter milk and skimmed milk powder, with ether or acetone (JP-A-03-47192), a method of adjusting butter milk to an acidic range, removing protein generated by isoelectric precipitation, and drying the concentrate obtained by subjecting the resultant supernatant to a microfilter membrane treatment (JP-B-3103218), and the like.

Furthermore, a method of coagulating and removing protein from butter serum, then subjecting the resultant to filtration and concentration, and drying the concentrate (JP-A-2007-89535) can be employed. For example, this preparation method makes it possible to prepare a fat globule membrane component containing 20% by mass or more of complex lipid derived from milk in terms of dry matter. Note here that the form of the fat globule membrane component is not particularly limited and the form may be liquid, semisolid and solid, powdery, and the like, and these forms may be used alone or in combination of two or more thereof.

Furthermore, as the fat globule membrane component, commercially available products may be used. Examples of such commercially available products include "BSCP" produced by MEGGLE JAPAN, "Milk Ceramide MC-5" produced by Snow Brand Milk Products Co., Ltd, and "Phospholipid Concentrate series (500, 700)" produced by New Zealand Milk Products.

Furthermore, since the fat globule membrane component is contained much in butter milk obtained when butter grains are produced from cream obtained by centrifugation of milk and the like, butter milk itself may be used. Similarly, since the fat globule membrane component is contained much in butter serum generated when butter oil is produced, butter serum itself may be used.

As described in the below-mentioned Examples, since the fat globule membrane component of the present invention significantly improved voluntary locomotor activity and significantly increased muscle strength of the soleus muscle in mice, the fat globule membrane component has a motor function improving action and a muscle strength improving action. Furthermore, since the fat globule membrane component of the present invention improved swimming endurance, the fat globule membrane component has an endurance improving action and an anti-fatigue action. Furthermore, since the fat globule membrane component of the present invention significantly increased the glycogen content in the skeletal muscle and significantly increased the expression amount of genes related to a muscle pump function in mice, the fat globule membrane component has a glycogen accumulation promoting action and a muscle pump function improving action.

Therefore, the fat globule membrane component can be used in a method of improving motor function in exercises as well as broadly-defined exercises including daily performance and labor by administration or intake of the fat globule membrane components in animals including humans.

In the present invention, motor function improvement refers to not only improving the motor ability of athletes and sports lovers, but also improving the physical activity level in persons whose motor organ function is reduced due to the onset of muscle atrophy or locomotive syndrome and the like, via improvement in muscle strength, endurance, or the like. Note here that the locomotive syndrome refers to a syndrome in motor organ, which is thought to be caused by motor organ dysfunction related to diseases in the motor organ itself or aging. Examples of the motor organ dysfunctions related to aging include muscle strength deterioration, endurance deterioration, prolonged reaction time, deterioration in movement speed, deterioration in skillness, bathyhypesthesia, and balance ability deterioration. Furthermore, insufficient exercise in addition to the aging may cause deterioration in entire motor organ function in addition to the above-mentioned deterioration in muscle strength or balance ability, thus causing problems such as a tendency to fall. Therefore, the fat globule membrane component of the present invention can be used to treat locomotive syndrome or sarcopenia, specifically, can be used to reduce the risk of developing, prevent or improve locomotive syndrome, and reduce the risk of developing, prevent or improve sarcopenia.

Furthermore, the fat globule membrane component can be used in a method for endurance improvement, anti-fatigue, muscle strength improvement, promoting of glycogen accumulation, or muscle pump function improvement in exercises as well as broadly-defined exercises including daily performance and labor by administration or intake of the fat globule membrane components in animal including humans.

Furthermore, the fat globule membrane component can be used as a motor function improver, an endurance improver, an anti-fatigue agent, a muscle strength improver, a glycogen accumulation promoting agent, and a muscle pump function improver (hereinafter, referred to as "motor function improver, and the like"), and can be further used to manufacture these agents. At this time, as the motor function improver and the like, the fat globule membrane component may be used alone, or in combination with appropriately selected additives such as a carrier and a stabilizing agent which are acceptable to the below-mentioned target materials, if necessary. Note here that the improver and the like can be produced by conventional methods depending upon the target materials to be blended.

Then, the motor function improver and the like, can be used as active ingredients to be blended in drugs, quasi drugs, foods, or feeds for humans or animals, which exhibit a motor function improving effect, an endurance improving effect, an anti-fatigue effect, a muscle strength improving effect, a glycogen accumulation promoting effect, or a muscle pump function improving effect. Furthermore, the fat globule membrane component has the concept of achieving motor function improvement, endurance improvement, anti-fatigue, muscle strength improvement, glycogen accumulation promotion, or muscle pump function improvement in persons with insufficient exercise, middle aged and older persons, persons who need bed rest, or athletes, and the fat globule membrane component can be applied for foods, functional foods, patient foods, foods for specified health, to which the concept is presented as needed.

The forms of administration of the motor function improver and the like according to the present invention used for active ingredients of drugs or quasi drugs include oral administration such as by tablets, capsules, granules, powders and syrups, and parenteral administration such as by injections, suppositories, inhalation drugs, transdermal systems, and external preparations. Furthermore, when preparations in such various dosage forms are prepared, the motor function improver and the like according to the present invention can be used alone or appropriately in combination with a pharmaceutically acceptable excipient, binder, extender, disintegrant, surfactant, lubricant, dispersing agent, buffering agent, preservative, corrigent, flavor, coating agent, carrier and diluent, and active ingredients other than the fat globule member component. Among these forms of administration, oral administration is preferred. A liquid preparation for oral administration can be prepared by a conventional method by addition of a corrigent, a buffering agent, a stabilizing agent, and the like.

When the motor function improver and the like according to the present invention are used for active ingredients of foods, they can be used in the forms of various foods such as foods and drinks and nourishing foods. Examples of such foods include cow milk, processed milk, milk beverages, yoghurt, refreshing beverages, tea beverages, coffee beverages, fruit juice beverages, carbonated drink, juice, jelly, wafer, biscuits, bread, noodles, and sausage. In addition, the examples include a nutrient supplying composition having the same forms as the above-mentioned oral administration preparation (tablets, capsules, syrups, and the like).

When various forms of foods are prepared, the motor function improver and the like according to the present invention may be used alone or appropriately in combination with other food materials or a solvent, a softener, an oil, an emulsifying agent, an antiseptic, a flavor, a stabilizing agent, a colorant, an antioxidant, a moisturizing agent, a thickening agent, and active ingredients other than the fat globule membrane component, and they may be blended in a motor function improving foods, endurance improving foods, anti-fatigue foods, muscle strength improving foods, pet foods, and the like.

Furthermore, the motor function improver and the like according to the present invention can be blended as a nutritional composition such as an enteral nutrient for aged persons or patients who need bed rest, who have difficulty in taking an adequate amount of nutrients.

When the motor function improver and the like according to the present invention are used as active ingredients of feeds, the same forms as the above-mentioned foods can be employed.

The content of the fat globule membrane component (in terms of dry matter) with respect to the above-mentioned beverages such as milk beverages, refreshing beverages, and tea beverages is generally 0.001 to 3.0% by mass, preferably 0.01 to 2.0% by mass, and more preferably 0.1 to 1.0% by mass.

In the case of foods or feeds or drugs which are other than the above, for example, oral solid preparations such as tablets, granules, and capsules, oral liquid preparations such as internal liquids and syrups, the content of the fat globule membrane component (in terms of dry matter) with respect to each of the total amount of the foods or feeds or drugs other than the above is generally 0.02 to 80% by mass, preferably 0.2 to 75% by mass, and more preferably 2 to 50% by mass. Note here that the state of the fat globule membrane component is not particularly limited and may be dissolved or dispersed.

The amount of administration or intake of the motor function improver and the like according to the present invention differs depending on the dosage forms or uses, but the daily dosage for an adult individual of the fat globule membrane component (in terms of dry matter) is preferably set at from 10 to 10000 mg/60 kg body weight. Specifically, the daily dosage is preferably set at from 100 to 5000 mg/60 kg body weight, and more preferably at from 500 to 5000 mg/60 kg body weight. Furthermore, the motor function improver and the like can be administered in an arbitrary administration/intake regimen, and administration/intake is preferably carried out once to several times per day.

The motor function improver and the like according to the present invention is preferably administered or taken during physical activity although the timing is not particularly limited. In particular, exercise is preferably combined with the administration or intake. When exercise is combined, the motor function improver and the like according to the present invention are preferably taken within from one hour before the exercise to one hour after the exercise. The exercises to be combined include exercises with strength capable of suppressing deterioration in muscle strength or with strength capable of improving muscle strength when such exercises are continued.

Furthermore, the above-mentioned preparation is administered or taken preferably three days or more per week, more preferably five days or more per week, and even more preferably every day. Furthermore, the duration of administration or intake is preferably two weeks or longer and more preferably four weeks or longer.

Subjects of administration or intake are not particularly limited as long as they are in need thereof. However, since the motor function improver and the like according to the present invention can improve the motor function, they are administered or taken effectively for in particular, sports lovers or athletes, persons with locomotive syndrome, persons with sarcopenia, persons with nervous/muscle diseases (inflammatory muscle diseases, myopathy associated with medical diseases, muscular dystrophy, congenital myopathy, mitochondrial encephalomyopathy, glycogen storage disease, and the like), persons who are physically inactive, persons who need bed rest, persons who undergo rehabilitation training after surgical/medical diseases.

EXAMPLES

Test Example 1

An effect of a fat globule membrane component on voluntary locomotor activity and improvement in muscle strength was examined. As the fat globule membrane component, BSCP produced by MEGGLE JAPAN was used (Table 1: Feed Composition).

BSCP contained, in terms of dry matter, 49% by mass (hereinafter, referred to as "%") protein, 39% lipid, 3.7% sphingomyelin as sphingophospholipid, 2.4% glucosylceramide and 0.4% ganglioside as glycosphingolipid.

An analysis method of protein and lipid in the fat globule membrane component was carried out by the Kjeldahl method (Kandatsu Makoto, Saishin Shokuhin Bunseki-Ho (Latest Analysis of Foods), Dobunshoin) and the Roese-Gottlieb method (Japan Society for Food Engineering, Shokuhin Bunseki-Ho (Food Analysis Method), Korin Publishing Co., Ltd).

Furthermore, an analysis of phospholipid in the fat globule membrane component was carried out by an LC-MS method. That is to say, a lipid fraction was extracted from the fat globule membrane component by using chloroform/methanol (=2:1), dried and hardened under a stream of nitrogen, and then dissolved in hexane/isopropanol (=95:5). This sample was subjected to the below-mentioned LC-MS analysis, and phospholipid was quantified.

As specific analysis means, the followings were used.
Column: Inertsil SIL 100A-3 (GL Science, 1.5 mm×150 mm)
Column temperature: 40° C.
Flow rate: 0.1 mL/min
Detector: Agilent, 1100 LC/MSD
Mobile phase: gradient separation of a liquid A (hexane:isopropanol:formic acid=95:5:0.1) and a liquid B (hexane:isopropanol:50 mM ammonium formate=25:65:10)

After preliminary rearing for one week, seven-week old BALE/c male mice were classified into two groups such that each group had the same body weight and voluntary locomotor activity. Each group was referred to as a Cont (normal diet) group and an MFGM (fat globule membrane component diet 1) group (n=6 in each group). Four weeks after grouping, voluntary locomotor activity of mice was measured by using a voluntary locomotor activity measurement apparatus equipping a cage with a running wheel, SW-15 (Melquest Inc). After four weeks of rearing, the mice were subjected to anatomy, and muscle strength of the soleus muscle was measured. Muscle strength of the isolated muscle was measured according to a method by Cannon et al. (Biomed Sci Instrum, 2005). That is to say, the soleus muscle was isolated from a mouse, fixed to a transducer (WPI, FORT100) by using suture (#5-0 silk), and immersed in a 37° C. Krebs solution (95%-$O_2$, 5%-$CO_2$ aeration). Electrical stimulation was carried out by using two platinum electrodes. In the stimulation, a single pulse (twitch) was applied, then stimulation at 40 Hz for 330 ms (1/s) was repeated for two minutes (120 seconds) (tetanic), and a signal (g/mg muscle) obtained from the transducer was determined as muscle strength. The significance test between the Cont group and the MFGM group was carried out by repeated measure ANOVA (voluntary locomotor activity) or Student's t-test (muscle strength).

TABLE 1

| Feed Composition (g/100 g) | | |
|---|---|---|
|  | Normal Diet | Fat Globule Membrane Component Diet 1 |
| Casein | 20 | 20 |
| DL Methionine | 0.2 | 0.2 |
| TAG | 10 | 10 |
| α-Potato Starch | 55.5 | 52 |
| Cellulose | 8.1 | 8.1 |
| Mineral (AIN-76 composition) | 4 | 4 |
| Vitamin (AIN-76 composition) | 2.2 | 2.2 |
| BSCP (MEGGLE JAPAN) |  | 3.5 |
| Total | 100 | 100 |

Figure 2:
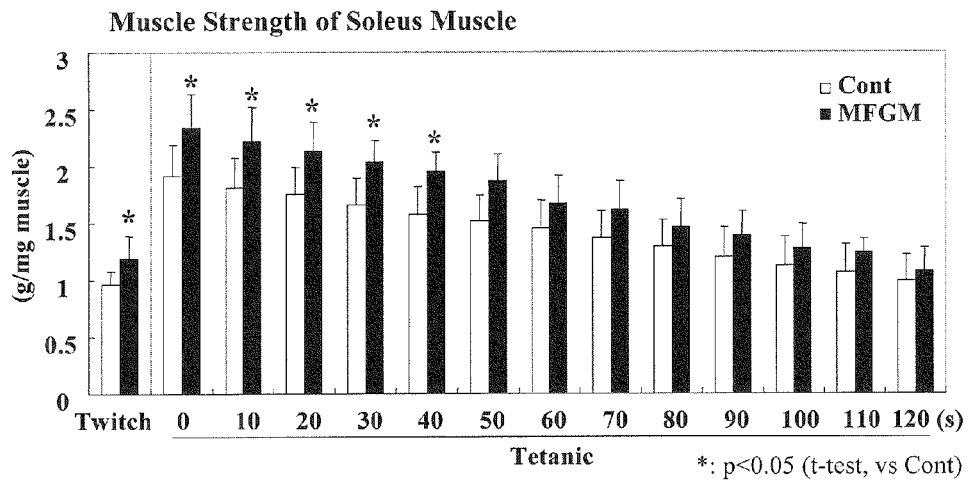
FIG. 2 is a graph showing muscle strength of the isolated soleus muscle. Cont represents a normal diet group, and MFGM represents a 3.5% fat globule membrane component diet group.

As a result, the MFGM group showed a significantly higher value than the Cont group in voluntary locomotor activity during a period (FIG. 1). Furthermore, the MFGM group showed a significantly higher value than the Cont group in muscle strength (FIG. 2).

The voluntary locomotor activity is the sum of motor function such as endurance and muscle strength. It is thought that improvement in the motor function improves the resistance to physical fatigue. In this test, since the fat globule membrane component increased the voluntary locomotor activity and the muscle strength of the isolated muscle, it was revealed that the fat globule membrane component is effective for improvement in motor function, endurance, and muscle strength, and anti-fatigue.

Test Example 2

An effect of a fat globule membrane component on endurance was examined. As the fat globule membrane component, Phospholipid Concentrate 700 produced by New Zealand Milk Products was used (Table 2: Feed Composition).

Phospholipid Concentrate 700 contained 85% lipid and 16.5% sphingomyelin in terms of dry matter.

After preliminary rearing for one week, seven-week old BALB/c male mice were classified into three groups such that each group had the same body weight and limit swimming time (=swimming endurance). Each group was referred to as an Ex (normal diet+exercise) group, an ML (1% fat globule membrane component diet 2+exercise) group, and an MH (3.5% fat globule membrane component diet 3+exercise) group. Swimming endurance was determined by measuring a swimming time to the utmost limit in a flowing water pool for mice (Kyodai Matsumoto type flowing water tank for measuring an amount of exercise). After grouping, test feed was fed and swimming training (5 L/min, 30 min) was given twice a week. Furthermore, at week 12 of rearing, the limit swimming time was measured, and an effect of the fat globule membrane component on endurance was examined.

Figure 3:
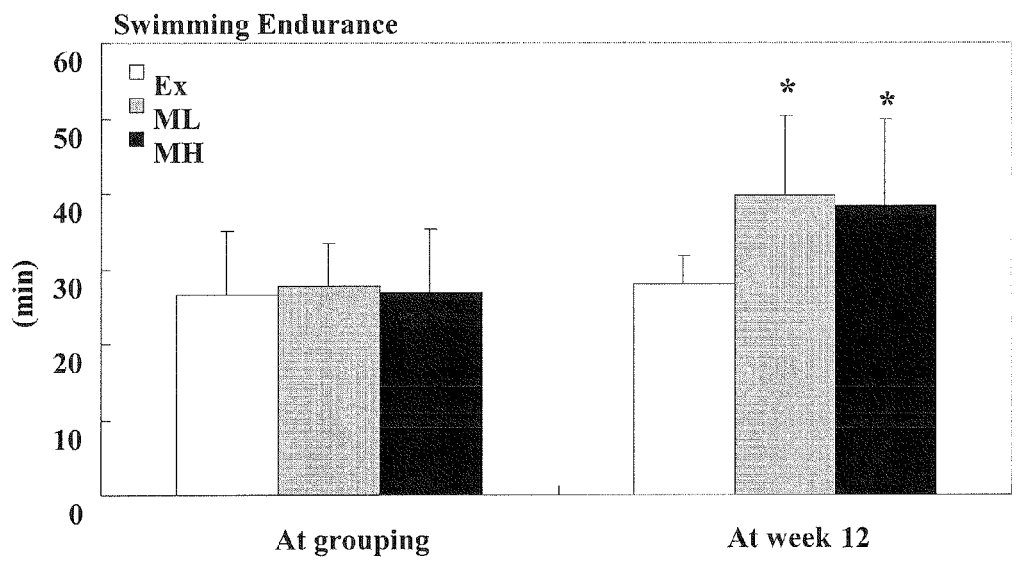
FIG. 3 is a graph showing swimming endurance. Ex represents a normal diet and exercise (exercise control) group, ML represents a 1% fat globule membrane component diet and exercise group, and MH represents a 3.5% fat globule membrane component diet and exercise group.

FIG. 3 shows a result of swimming endurance at the time of grouping and at week 12. The swimming times of the ML group and the MH group showed significant higher values than the Ex group.

TABLE 2

Feed Composition (g/100 g)

|  | Normal Diet | 1% Fat Globule Membrane Component Diet 2 | 3.5% Fat Globule Membrane Component Diet 3 |
| --- | --- | --- | --- |
| Casein | 20 | 20 | 20 |
| DL Methionine | 0.2 | 0.2 | 0.2 |
| TAG | 10 | 10 | 10 |
| α-Potato Starch | 55.5 | 54.5 | 52 |
| Cellulose | 8.1 | 8.1 | 8.1 |
| Mineral (AIN-76 Composition) | 4 | 4 | 4 |
| Vitamin (AIN-76 Composition) | 2.2 | 2.2 | 2.2 |
| Phospholipid Concentrate 700 (New Zealand Milk Products) |  | 1 | 3.5 |
| Total | 100 | 100 | 100 |

From the results, it was revealed that the fat globule membrane component is effective for improvement in exercise endurance. Furthermore, since the improvement in exercise endurance means improvement in the physical fatigue resistance, it was revealed that the fat globule membrane component is effective for anti-fatigue.

Test Example 3

An effect of a fat globule membrane component on a glycogen content in the skeletal muscle and gene expression was examined. As the fat globule membrane component, Milk Ceramide MC-5 produced by Snow Brand Milk Products Co., Ltd was used (Table 3: Feed Composition). Milk Ceramide MC-5 contained 21.2% protein and 59.3% lipid and 6.9% sphingomyelin in terms of dry matter.

TABLE 3

Feed Composition (g/100 g)

|  | Normal Diet | Fat Globule Membrane Component Diet 4 |
| --- | --- | --- |
| Casein | 20 | 20 |
| DL Methionine | 0.2 | 0.2 |
| TAG | 10 | 10 |
| α-Potato Starch | 55.5 | 54.5 |
| Cellulose | 8.1 | 8.1 |
| Mineral (AIN-76 composition) | 4 | 4 |
| Vitamin (AIN-76 composition) | 2.2 | 2.2 |
| MC-5 (Snow Brand Milk Products Co., Ltd) |  | 1 |
| Total | 100 | 100 |

After preliminary rearing for one week, seven-week old BALB/c male mice were classified into four groups such that each group had the same weight and limit swimming time (=swimming endurance). Each group was referred to as a Cont (normal diet) group, an MF (1% fat globule membrane component diet 4) group, an Ex (normal diet+exercise) group, and an MF-Ex (1% fat globule membrane component diet 4+exercise) group. After grouping, the mice were fed with test feed. To the Ex group and the MF-Ex group, swimming training (5 L/min, 30 min) was given twice a week, and to the Cont group and the MF group, swimming training was not given.

At week 12 of rearing, a limit swimming time of each group was measured. Thereafter, at week 13 of rearing, the mice were subjected to anatomy, muscle strength of the soleus muscle was measured. After anatomy, a glycogen content in the gastrocnemius muscle was measured according to a method by Xu et al. (J Cell Mol Med, 942-54, 2008), and the expression amounts of genes of $Na^+$—$K^+$ pumpβ1 and SERCA2 in the soleus muscle and the gastrocnemius muscle were measured by a quantitative PCR method (Murase et al., Biogerontology, 2009). Primers used when the expression amount of genes related to the muscle pump function was measured are shown in Table 4 (SEQ ID NOs: 1 to 6). It is known that the $Na^+$—$K^+$ pumpβ1 is a gene related to Na pumping function, and SERCA2 (sarcoplasmic/endoplasmic reticulum $Ca^{2+}$ ATPase) is a gene related to Ca pump.

TABLE 4

| Name of Gene | Accession # | Forward Primer | Reverse Primer |
| --- | --- | --- | --- |
| 36B4 | NM_007475 | GACATCACAGAGCAGGCCCT | TCTCCACAGACAATGCCAGG |
| Na-K pump β1 | NM_009721 | GCTGGCCGTGCAGTTCA | CACTCGACGCGGATTTCAG |
| SERCA2 | NM_009722 | TACTGACCCTGTCCCTGACC | CACCACCACTCCCATAGCTT |

As a result, at week 12 of rearing, the limit swimming time showed a significantly higher value in the MF-Ex group (52.6 (4.5 min)) than in the Ex group (40.1 (3.8 min)), showing that endurance was improved by taking the fat globule membrane component diet. Furthermore, at week 13 of rearing, in muscle strength of the soleus muscle, the MF-Ex group showed 1.90 (0.08 g/mg muscle), the Ex group showed 1.73 (0.07 g/mg muscle), Cont group showed 1.64 (0.07 g/mg muscle), showing that muscle strength was improved by taking the fat globule membrane component diet.

Figure 4:
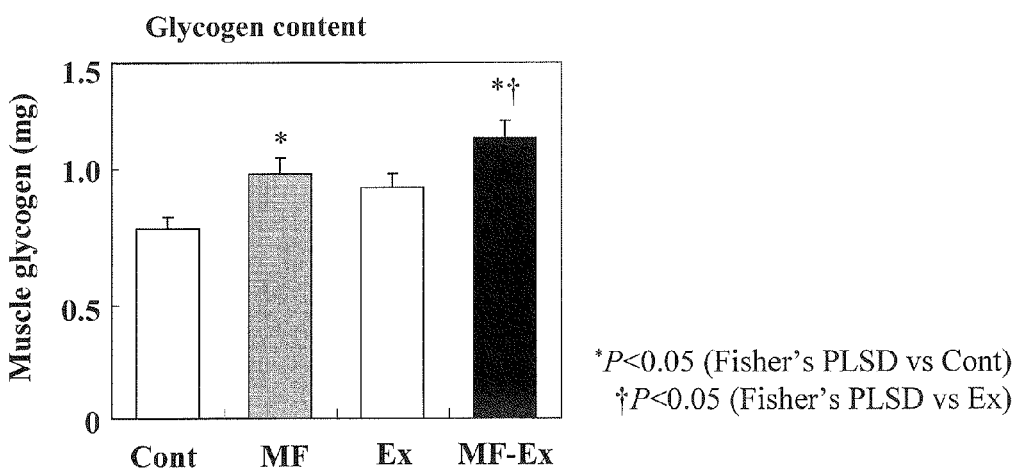
FIG. 4 is a graph showing a glycogen content in the gastrocnemius muscle. Cont represents a normal diet (control) group, MF represents a 1% fat globule membrane component diet group, Ex represents a normal diet and exercise (exercise control) group, and MF-Ex represents a 1% fat globule membrane component diet and exercise group.

FIG. 4 shows a glycogen content in the gastrocnemius muscle at the time of anatomy. The MF group and the MF-Ex group showed a significantly high value of muscle glycogen. Therefore, it was revealed that the fat globule membrane component had a promoting effect on accumulation of muscle glycogen. Since glycogen in the muscle is an important energy source for muscle contraction, it is thought that the increase in the muscle glycogen amount by taking the fat globule membrane component contributes to the improvement in the motor function.

Figure 5:
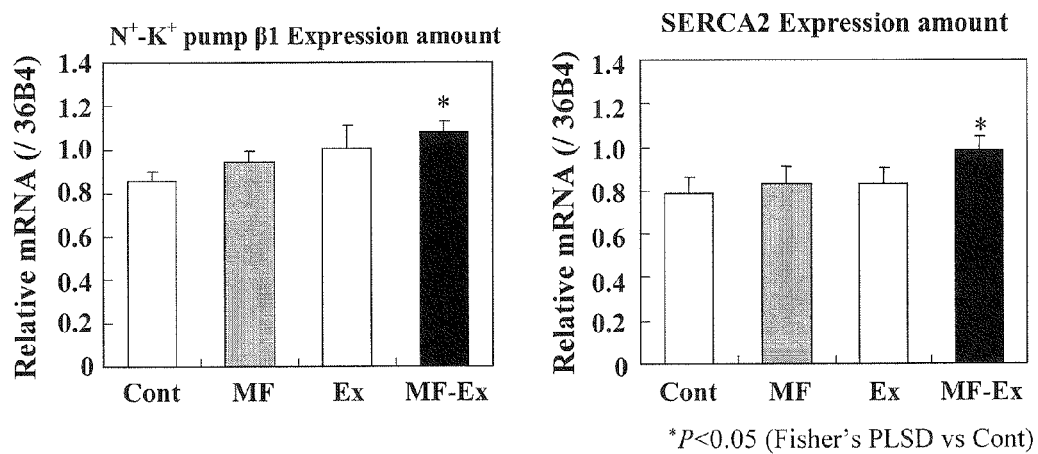
FIG. 5 is a graph showing gene expression amounts of $Na^+$—$K^+$ pump$\beta 1$ (Na pump) and SERCA2 (Ca pump) in the soleus muscle. Cont represents a normal diet (control) group, MF represents a 1% fat globule membrane component diet group, Ex represents a normal diet and exercise (exercise control) group, and MF-Ex represents a 1% fat globule membrane component diet and exercise group. Relative mRNA (/36B4) shows a relative mRNA expression amount obtained by correcting an expression amount of the obtained gene by using the expression amount of the housekeeping gene 36B4.

FIG. 5 shows results of expression amount of genes related to the muscle pump function in the soleus muscle at the time of anatomy. The MF group showed higher values of the expression amounts of $Na^+$—$K^+$ pumpβ1 (Na pump) and SERCA2 (Ca pump) than the Cont group, and the MF-Ex group showed higher values of the expression amounts of $Na^+$—$K^+$ pumpβ1 (Na pump) and SERCA2 (Ca pump) than the Ex group. In particular, the MF-Ex group showed significantly higher values of the expression amounts of $Na^+$—$K^+$ pumpβ1 (Na pump) and SERCA2 (Ca pump) than the Cont group. It is known that the Na pump is involved in maintaining the excitability of myocyte membrane via action potential duration and that the Ca pump is involved in taking calcium into the sarcoplasmic reticulum. Both have an important role in the muscle contraction/muscle strength exhibition. Therefore, it was revealed that the fat globule membrane component is effective as the muscle pump function improver, and acts on improvement in motor function such as endurance and muscle strength through improvement in pump function related to muscle contraction.

Preparation Example

Formulation Example 1

Motor Function Improving Jelly Foods

A mixture was obtained from a 0.65% mixed gelling agent of carrageenan and Locust bean gum, 5.0% concentrated fruit juice of 50% grapefruit, 0.05% citric acid, 0.05% vitamin C, and a 2.0% fat globule membrane component (Phospholipid Concentrate 700 produced by New Zealand Milk Products: 85% lipid, 16.5% sphingomyelin). Water was added to the mixture so as to adjust to 100%, and the mixture was dissolved in the water at 65° C. Furthermore, to the mixture solution, a small amount of a grape fruit flavor was added, and the mixture solution was held for five minutes at 85° C. to carry out sterilization. Then, the mixture solution was dispensed into 100 mL vessels. The mixture was allowed to stand for eight hours while it was gradually cooled to 5° C. and gelled to obtain a jelly food containing the fat globule membrane component and having good solubility in the mouth, fruit flavor, and good texture.

Formulation Example 2

Motor Function Improving Tablet

A tablet was produced by formulation (daily dosage: 2200 mg) composed of 180 mg of ascorbic acid, 50 mg of citric acid, 12 mg of aspartame, 24 mg of magnesium stearate, 120 mg of crystalline cellulose, 274 mg of lactose, and 440 mg of a fat globule membrane component (BSCP produced by MEGGLE JAPAN: 49% protein, 39% lipid, 3.7% sphingomyelin, 2.4% glucosylceramide, and 0.4% ganglioside) according to Japanese Pharmacopoeia (General Rules for Preparation: "Tablets"). Thus, tablets containing the fat globule membrane component were obtained.

Formulation Example 3

Motor Function Improving Vitamin Oral Liquid

To an appropriate amount of purified water, 800 mg of taurine, 2000 mg of sucrose, 50 mg of caramel, 30 mg of sodium benzoate, 5 mg of vitamin B1 nitrate, 20 mg of vitamin B2, 20 mg of vitamin B6, 2000 mg of vitamin C, 100 mg of vitamin E, 2000 IU of vitamin D3, 20 mg of nicotinamide, 1000 mg of a fat globule membrane component (Milk Ceramide MC-5 produced by Snow Brand Milk Products Co., Ltd: 21.2% protein, 59.3% lipid, and 6.9% sphingomyelin), 200 mg of leucine, 100 mg of isoleucine, and 100 mg of valine were added and dissolved. The mixture solution was adjusted to pH 3 with an aqueous solution of phosphoric acid. Purified water was further added so that the total amount became 50 mL. The resultant was sterilized at 80° C. for 30 minutes to obtain a motor function improving beverage containing the fat globule membrane component and amino acids.

Formulation Example 4

Motor Function Improving Milk Beverage

Purified water was added to 3.4 g of milk casein, 1.67 g of isolated soybean protein, 14.86 g of dextrin, 1.3 g of sucrose, 1.75 g of soybean oil, 0.18 g of Perilla oil, 0.14 g of soybean phospholipid, 0.07 g of glycerine fatty acid ester, 0.60 g of minerals, 0.06 g of vitamins, and 1.0 g of fat globule membrane component (Phospholipid Concentrate 500 produced by New Zealand Milk Products: 89% lipid and 7.8% sphingomyelin). The mixture was subjected to retort sterilization according to an ordinary method to obtain a motor function improving beverage (100 mL) containing the fat globule membrane component.

What is claimed is:

1. A motor function improving method, comprising administering a fat globule membrane component to a subject in need of an improvement in said subject's motor function, or the taking of a fat globule membrane component by said subject.

2. An endurance improving method, comprising administering a fat globule membrane component to a subject in need of an improvement in said subject's endurance or the taking of a fat globule membrane component by said subject.

3. An anti-fatigue method, comprising administering a fat lobule membrane component to a subject in need of an anti-fatigue agent or the taking of a fat globule membrane component by said subject.

4. A muscle strength improving method, comprising administering a fat globule membrane component to a subject in need of an improvement in said subject's muscle strength or the taking of a fat globule membrane component by said subject.

5. A glycogen accumulation promoting method, comprising administering a fat globule membrane component to a subject in need of promoting said subject's glycogen accumulation or the taking of a fat globule membrane component by said subject.

6. A muscle pump function improving method, comprising administering a fat globule membrane component to a subject in need of improving said subject's muscle pump or the taking of a fat globule membrane component by said subject.

7. The motor function improving method according to claim 1, wherein said subject is a human.

8. The motor function improving method according to claim 7, wherein said subject is physically inactive.

9. The motor function improving method according to claim 1, wherein said subject has a nerve or muscle disease.

10. The motor function improving method according to claim 1, wherein said subject is also undergoing rehabilitation training.

11. A method for reducing a risk of developing, or improving locomotive syndrome, comprising administering a fat globule membrane component to a subject in need of reducing said subject's risk of developing locomotive syndrome, or in need of improving said subject's locomotive syndrome, or the taking of a fat globule membrane component by said subject.

12. A method for reducing a risk of developing, or improving sarcopenia, comprising administering a fat globule membrane component to a subject in need of reducing said subject's risk of developing sarcopenia, or in need of improving said subject's sarcopenia, or the taking of a fat globule membrane component by said subject.

13. The method of claim 11, wherein said subject is human.

14. The method of claim 12, wherein said subject is human.

15. The method of claim 7, wherein said human is an adult.

16. The method of claim 15, wherein the daily dosage of said fat globule membrane component that is administered to or taken by said adult is 10 to 10,000 mg per 60 kg body weight.

17. The method of claim 1, wherein said fat globule membrane component is administered to or taken by said subject within an hour before, during, or within an hour after, exercise.

18. The method of claim 1, wherein said fat globule membrane component is derived from cow's milk.

* * * * *